United States Patent
Hanuliak

(10) Patent No.: US 10,918,295 B2
(45) Date of Patent: Feb. 16, 2021

(54) SYSTEM AND METHOD FOR ECG SIGNAL PROCESSING

(71) Applicant: BTL Medical Technologies S.R.O., Prague (CZ)

(72) Inventor: Martin Hanuliak, Prague (CZ)

(73) Assignee: BTL MEDICAL TECHNOLOGIES S.R.O., Prague (CZ)

(*) Notice: Subject to any disclaimer, the term of this patent is extended or adjusted under 35 U.S.C. 154(b) by 61 days.

(21) Appl. No.: 15/899,751

(22) Filed: Feb. 20, 2018

(65) Prior Publication Data
US 2018/0168471 A1   Jun. 21, 2018

Related U.S. Application Data

(63) Continuation-in-part of application No. 15/159,104, filed on May 19, 2016, now abandoned.

(51) Int. Cl.
| A61B 5/04 | (2006.01) |
| A61B 5/0456 | (2006.01) |
| A61B 5/0472 | (2006.01) |
| A61B 5/00 | (2006.01) |
| A61B 5/0468 | (2006.01) |
| A61B 5/0408 | (2006.01) |

(52) U.S. Cl.
CPC ........ *A61B 5/04012* (2013.01); *A61B 5/0456* (2013.01); *A61B 5/0472* (2013.01); *A61B 5/742* (2013.01); *A61B 5/0408* (2013.01); *A61B 5/0468* (2013.01); *A61B 2503/10* (2013.01)

(58) Field of Classification Search
CPC ... A61B 5/0402; A61B 5/0452; A61B 5/0456; A61B 5/0472
See application file for complete search history.

(56) References Cited

U.S. PATENT DOCUMENTS

| 4,565,201 A * | 1/1986 | Lass .................. A61B 5/04004 600/509 |
| 5,178,154 A * | 1/1993 | Ackmann ............ A61B 5/0205 600/508 |
| 2012/0089037 A1 * | 4/2012 | Bishay ................ A61B 5/0404 600/509 |
| 2016/0001070 A1 * | 1/2016 | Fahey ................. A61N 1/0476 600/509 |
| 2016/0331273 A1 | 11/2016 | Armoundas |

FOREIGN PATENT DOCUMENTS

WO   2012016729 A1   2/2012

* cited by examiner

*Primary Examiner* — Allen Porter
(74) *Attorney, Agent, or Firm* — Riverside Law LLP

(57) ABSTRACT

Methods and systems provide for quick and precise analysis of ECG data, with a simple and understandable visualization and an effective way of communicating the proposed diagnosis suggestion to the medical personnel. Systems and methods detect electrical potentials from at least one lead and process at least one signal. The measurement itself may be executed on the raw signal, to compare measured parameters with a set of criterions related to various diseases, for example to sudden death syndrome.

20 Claims, 6 Drawing Sheets

SYSTEM AND METHOD FOR ECG SIGNAL PROCESSING

PRIORITY CLAIM

This Application is a continuation-in-part of U.S. patent application Ser. No. 15/159,104 filed May 19, 2016 and now pending, which is incorporated herein by reference in its entirety.

FIELD OF INVENTION

The present invention relates to a method and system for the automatic processing of signals representing the electrical activity of heart. Methods and systems provide for electrocardiography data interpretation in shorter time with improved measuring means and visualization of signal.

BACKGROUND

The electrocardiography ("ECG") measures the electrical activity of the heart using electrodes placed on a body. The activity is measured over a period of time and reflects the direction of electrical current generated by a depolarization and a repolarization of cardiac cells. Heart activity may be tracked by a conventional system of three, five, seven twelve or sixteen leads, although even different numbers might be used.

A conventional 12-lead ECG captures tracing of the electrical activity from 12 different views of the heart muscle. The 12-leads include three bipolar limb leads, three unipolar augmented limb leads and six unipolar chest leads. This type of ECG also records the mean instantaneous vector representing the force and direction of the wave of the depolarization and repolarization through the heart. The mean instantaneous vector is also called the electrical axis.

Besides the 12-lead conventional system, other systems with various numbers of electrodes may be used to monitor the electrical activity of the heart muscle.

The recorded ECG signal is represented by a number of waves generated by individual leads. The ideal wave refers to a series of beats, which are represented by waveforms, where the deflections are typically marked as PQRST. Sixth and subsequent components, e.g. a U waveform may be visible under certain conditions. These deflections show flow of electric impulses through the heart.

Waveform analysis, referred to as a measurement, provides a set of parameters for every beat which may point towards deviations in the function of the cardiac muscle. The ECG parameters determined by the measurement are frequently used to determine a diagnosis of the heart muscle.

The recorded ECG signal may be recorded on graph paper as an analog signal. Analysis of this signal is slow and makes precise measurement of parameters difficult. The ECG signal may be also visualized as a digitalized signal, where the plurality of beats may be averaged to provide an averaged beat. In fact, the averaging of the beats to provide an averaged beat is a standard procedure of signal digitalization. The analog report does not provide an averaged report.

The ECG signal recorded by the plurality of leads is usually averaged by spatial or temporal averaging to produce a beat representing an average shape of all beats. Both techniques are based on the assumption that noise is random, whereas the signal has repetitive characteristics. Spatial averaging originates from multiple inputs by use of multiple closely spaced electrode pairs placed on the body. These inputs are averaged to provide noise reduction. Spatial averaging is able to provide an averaged ECG from a single beat, allowing a real-time beat-to-beat analysis, but requires electrical shielding of the patient. A second methodology, namely temporal averaging, uses a large number of beats (typically 10 or more). The digitalized beats are aligned and averaged with a recognition template to reject noisy beats. As a result the averaged signal cancels noise, which can be described as a number of electrical impulses that do not occur as a repetitious pattern or with the same consistent timing as the representative beat. However, a problem of the averaging methods is that it leads to loss of part of the information and increases the possibility of a wrong diagnosis. In some cases, automated ECG fails substantially in comparison to the manual approach.

The recorded signal is often interpreted using an ECG paper report. Parameters, which are capable of providing a diagnostic suggestion of a cardiac disease, are measured by many manual and time-consuming techniques from every single waveform, single beat or plurality of beats originating from every individual lead. Although the manual method may be preferred among general medical personnel, satisfactory execution of the analysis requires skill. The prolonged time of analysis and required skills when using the traditional measuring methods, in a stressful medical practice, may result in a wrong diagnosis. Also, visualization of the recorded signals on simple graph paper does not allow exact comparison of beats by the naked human eye.

For example, important QRS deflections may have different shapes on every lead and they may not start from the same spot on the different leads. Although the ISO standard provides the types of the leads used for localization of the QRS deflections, it is difficult and time consuming to follow due to the need of knowledge of different standards of various patients and diseases. This may lead to non-uniformity of the ECG analysis executed by different hospital departments. In addition, the location of the QRS deflection is an important difference between young healthy people and adults and sick patients.

In another example, the T deflection of one beat may partially overlap the P deflection of the following beat, therefore the T deflection does not reach the baseline and both deflections are not separated. This example can be observed predominantly on the ECG signal of young populations, but it may also occur in others.

Measurement of the non-averaged ECG signal and/or evaluation of the parameters may point towards a number of heart diseases, including arrhythmias, suspected heart attacks, seizures, ischemia, hypertrophies, myocardial blocks, and others.

The ECG analysis may be also used to predict the possibility of sudden cardiac death. One of the proposed set of criterions is designed for athletic youth. The set of standardized criterions is defined on the parameters measured on the ECG waves derived from individual leads of the conventional 12-lead ECG system. As a result, averaged ECG cannot be used for the loss of information during the signal averaging. A similar set of criterions was proposed for a diagnosis of Brugada syndrome and other serious diseases.

In light of the above, it is desired to provide a method and system for quick measurement and analysis of ECG raw data in order to analyze a large set of criterions and visualization of the calculated parameters with visualized limits of the predetermined criterions to allow medical personnel to evaluate the level of parameter breaching.

SUMMARY OF INVENTION

Methods and systems provide for quick and precise analysis of ECG data, with a simple and understandable visualization and an effective way of communicating the proposed diagnosis suggestion to the qualified person. Systems and methods detect the electrical potentials from at least one lead and process at least one signal without any type of averaging. The measurement itself may be executed on the raw signal, to compare measured parameters with a set of criterions related to various diseases, for example to sudden death syndrome.

Heart activity may be tracked by a conventional system of three, five, seven, twelve or sixteen leads. The system is not limited to the particular number of the leads, but it may consist of any other number of leads. The signal is subjected to a measurement, where the parameters are calculated and compared to a predefined set of criterions. A proposed diagnosis suggestion is based on a predetermined set of criterions, which may aid the qualified person in a selection of the precise diagnosis. The qualified person may check, adjust and/or change the parameter measurement to asses or correct the level of at least one criterion breach and in order to influence the diagnosis proposal.

According to another embodiment the qualified person may add at least one new criterion to the already existing set of criterions to make a precise proposed diagnosis.

According to still another embodiment the qualified person may create a new set of criterions to adapt the system and method for providing a diagnosis suggestion to any other disease or population of patients.

According to still another embodiment, a method selects a typical beat from plurality of beats of the certain lead, plurality of beats of all leads; and/or a selection of beats from any lead performed by qualified person.

Visualization of the parameters and displayed criterions of the parameters along with the diagnosis suggestion helps the qualified person to support or correct the possible diagnosis. In case of typical beat selection, the typical beat may be superimposed by at least one beat originating from the same lead. The typical beat may be also superimposed by at least one beat from another lead. For comparison, signals of additional beats may possess a certain degree of transparency according to their similarity to the typical beat.

In another embodiment, the typical beat may be zoomed-in to provide more detailed information. Also, the mathematical basis of every calculated parameter may be visualized together with the related measuring instrument, which may contain colored parts to distinguish the severity of breach of at least one criterion from a set of criterions. The rulers may also show border lines demonstrating the measurement of normality/abnormality and therefore it shows the part of the ECG signal potentially not meeting the limits of criterions.

The invention also extends the utility of ECG to various parts of population. The independence of the present invention from any type of reference allows detection of possible heart diseases on different groups of people, e.g. athletic youth, sporting population and people living with high-altitude adaptation. The selection of the typical beat provides the analysis of the ECG signal of different types of people. Their ECG signal may be atypical by the influence of many factors, for example breathing. When the typical beat is selected from the plurality of the recorded beats, the influence of the environment or the patient is not manifested on the ECG analysis.

Glossary

The term "signal" means a curve representing electrical potential recorded by at least on ECG lead.

The term "parameter" means a measurable factor that describes at least one characteristic of at least one signal and/or wave entity (e.g. distance between wave deflections, amplitude or inclination).

The term "measurement" means a process of obtaining at least one parameter from at least one single beat or the entire ECG recorded signal.

The term "criterion" means at least one parameter restricted by limits. Usage of criterion results in diagnosis suggestion. Criterion may be predetermined by system and/or a qualified person.

The term "patient" means a human or animal.

The term "beat" means a signal wave's deflections PQRST or at least one deflection present on the ECG signal from at least one lead. The beat may be subjected to measurement.

The term "typical beat" means a beat or at least one of deflections selected from at least one lead by an algorithm according to selection attributes and/or by a qualified person.

The term "caliper" means a position mark on the displayed ECG signal defining at least one region of the signal.

All of the figures show examples and are not intended to be limits on the scope of the invention.

DETAILED DESCRIPTION

The principles and execution of the method and the apparatus may be better understood with reference to the drawings and the accompanying description of the non-limiting, exemplary embodiments.

Electrocardiography is a technique of recording the electrical activity of the heart muscle using electrodes placed on the body, where electrodes define leads. Individual leads provide a view of the electrical activity between a positive and negative pole. Heart electrical activity may be recorded by a conventional system of three, five, seven, twelve or sixteen leads. The system and method described below is not limited to mentioned number of the electrodes and leads, but it may consist of any other number of ECG leads and/or electrodes. In another embodiment, not all the leads connected to the patient may be required to be used in order to monitor ECG signal. In still another example, the electrodes may be placed in a special position to measure a derived ECG.

Figure 1A:
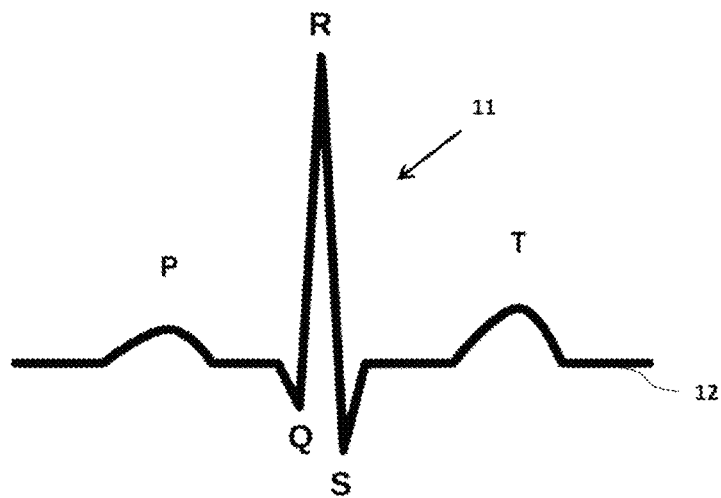
FIG. 1A is an illustration of an ECG recording that describes the various entities of a voltage signal of a normal heartbeat.

FIG. 1A shows a simplified representation of one beat 11 shown on ECG signal 12 recorded by an individual lead. The deflections forming the beat 11, marked PQRST (waves P, Q, R, S and T), represent flow of the electric impulses through the heart muscle. Deflection U, which may follow the T deflection, is not shown on this figure as it may not appear on every ECG signal 12. It should be noted that the shape and direction of the deflections may be different according to the type of the lead used to the ECG signal recording.

Figure 1B:
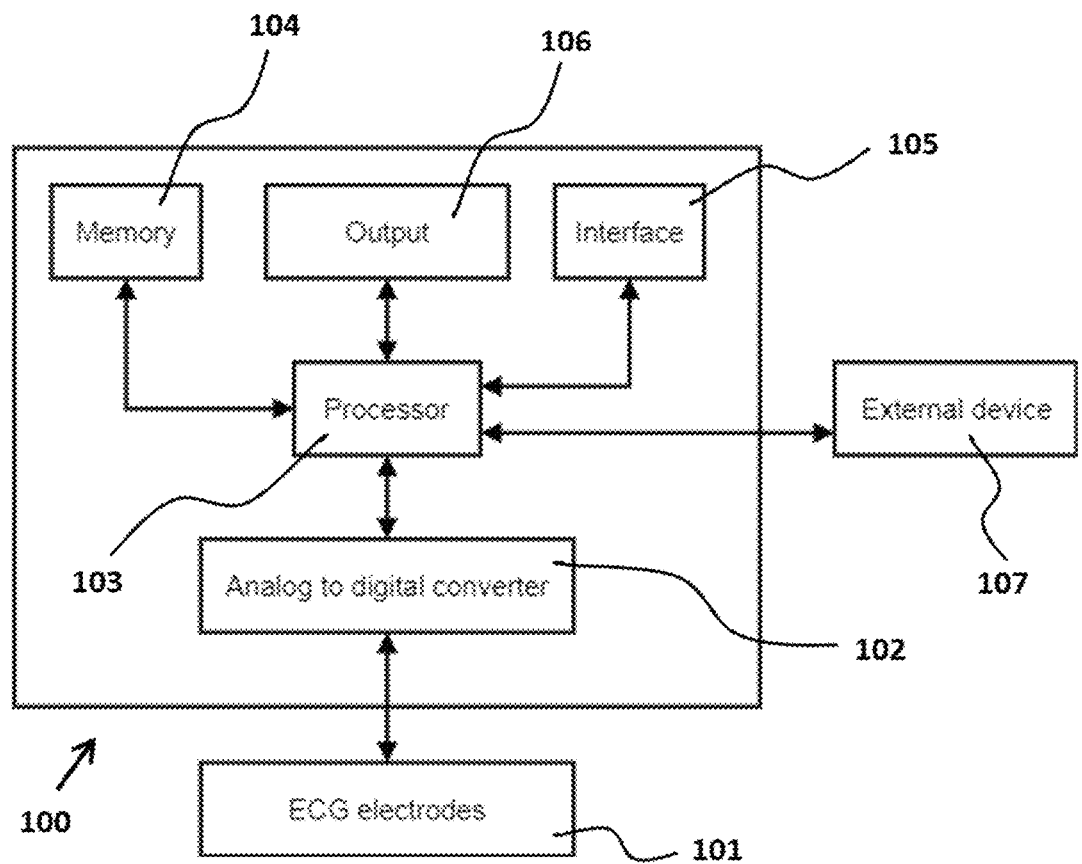
FIG. 1B is an exemplary diagram of an ECG monitoring system and an external device.

FIG. 1B shows an example for an ECG monitoring system 100, which may be any device e.g. computer, laptop, mobile phone, tablet or other general computing device integrating software and hardware. ECG monitoring system 100 may be connected to at least one ECG electrode 101. ECG monitoring system 100 may include an analog to digital converter 102, a processor 103, a memory 104, an interface 105 and/or an output 106. The processor 103 may communicate with memory 104, interface 105, output 106, analog to digital converter 102, at least one ECG electrode 101 an/or external device 107. The ECG monitoring system 100 may include an output 106 (e.g. LCD screen, display or printing device) capable of generating report of ECG data. The ECG monitoring system 100 may include interface 105 e.g. display unit displaying settings and/or status of ECG data recording.

ECG monitoring system may 100 be connected to at least one or more preferably three, six, twelve or sixteen electrodes. The electrodes may be disposed upon and/or within a surface of the patient's body. Electrodes may be coupled to at least one lead wire (not shown), which may provide ECG data to the analog to digital converter 102. The analog to digital converter 102 may convert recorded analog ECG data to digital ECG data, which may be then communicated to the processor 103. The processor 103 may communicate the ECG data to memory 104, output 106, interface 105 and/or external device 107.

ECG monitoring system 100 may operate standalone, as part of, or in collaboration with at least one external device 107 e.g. computer, laptop, server, mobile, portable device, wearable device (e.g. watch or bracelet), cloud and/or mainframe. The ECG monitoring device 100 may record ECG data which may be transmitted to the external device 107 using wires or wireless communication e.g. Bluetooth and/or wireless local area networking (Wi-Fi). The ECG data may be transmitted to external device 107 immediately after their recording or they may be stored in the memory 104. According to operator's wishes, the ECG data may be retrieved from the memory 104 later after their recording and analyzed by the ECG analysis process.

The ECG analysis process may be provided by ECG monitoring device and/or external device 107.

Method may include preparation of the patient, positioning of the electrodes 101, recording of the ECG signal, executing ECG analysis process and providing graphic representation.

Preparation of the patient may include shaving of the tissue and applying gel to increase adhesion of applied electrodes to the patient's tissue.

Positioning of the electrodes 101 may include application of the electrodes 101 into different positions on or into the patient's body. Placement of the electrodes 101 may be into positions providing a limb leads, Frank leads and/or 12-lead system. Placement of the electrodes 101 may be in 12-lead electrode placement. Also, electrodes may be positioned into orthogonal or non-orthogonal positions.

The 12-lead system may include six limb leads including I, II, III, augmented vector right ($aV_R$), augmented vector left ($aV_L$) and augmented vector foot ($aV_F$). Further, the 12-lead system may include six precordial leads—$V_1$, $V_2$, $V_3$, $V_4$, $V_5$ and $V_6$.

Figure 2:
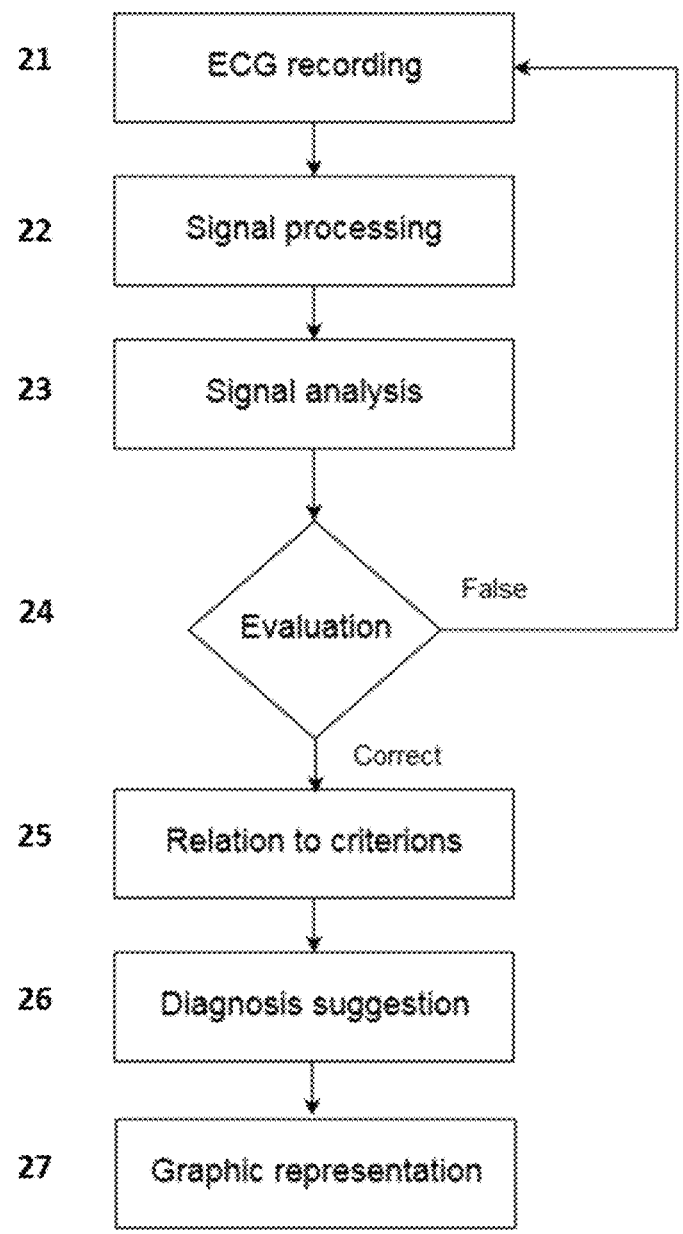
FIG. 2 is a block diagram illustrating a non-limiting example of a method.

FIG. 2 illustrates exemplary block diagram of the ECG analysis process. Recorded ECG data may be subjected to signal processing and signal analysis. Analyzed data may be then related to a predetermined set of criterions and the proposal of a diagnosis suggestion is provided to the qualified person.

ECG data recording 21 may be executed by at least a pair of electrodes and/or at least one unipolar electrode connected to the patient and/or all electrodes. In another embodiment, the signal recording may be preferably executed by a standard 12-lead system. Signal recording may last from 0.5 seconds to 3600 seconds. In another embodiment, it may last from 1 second to 1800 seconds. In still another embodiment, it may last from 5 seconds to 60 seconds. In still another embodiments it may last from 5 second to 20 seconds, 5 to 15 second or 8 second to 12 seconds. In another embodiment not all the connected leads may be used to detect an ECG signal. The ECG data recording may mean storing the data for further processing and analysis. Recorded data may also be stored in volatile or non-volatile memory or transferred to storage unit of a Hospital Information System for later use.

Signal processing 22 may include at least one of filtering, multiplication, exponentiation, correlation, derivation, integration, and the like. Filtering may remove unwanted components of the signal such as baseline drift, motion artifacts, muscle artefacts, power line interference and/or EMG from the chest wall. Signal processing may be executed in different times during and after the ECG data recording 21. For example, it may be executed during the data recording. This exemplary embodiment is advantageous during a stress test of the patient, when the qualified person may judge the results of the method before the end of the procedure. In another embodiment, the signal processing may be executed immediately after the data recording. In still another embodiment, the signal processing may be executed after the data recording.

Signal analysis 23 may include at least one of detection of the beats, measurement of the beats and/or selection of the typical beat. Beats may be detected by various methods and algorithms. In one embodiment the beats may be detected by application of an adaptive algorithm searching for the maxima of the signal. In another embodiment the beats may be detected by the comparison and/or combination of at least two leads and/or application of an adaptive algorithm searching for the global and/or local maxima of the signal. In still another embodiment, the beats may be detected by the combination of at least two, three or more leads providing the best signal and/or application of an adaptive algorithm searching for the global and/or local maxima of the signal. In still another embodiment, the beats may be detected by the combination of at least two selected ECG electrodes creating at least one lead signal and/or application of an adaptive algorithm searching for the global and/or local maxima of the signal. In still another embodiment, the beats may be identified by multiplication of the signal of an individual leads by itself and detection of the points with slope greater than a predefined slope threshold.

The beat detection may be followed by signal measurement, which may provide at least one parameter characterizing a detected ECG signal and/or detected deflections. The parameters may include P wave duration, PR interval duration, QT interval duration and any other parameter predefined by a system and/or qualified person. Signal measurement may be executed without any type of averaging process on a selection of beats described below. Therefore, the signal measurement may provide parameters of all available beats of all leads without any loss of information, as may happen by using averaging process.

The signal measurement of the parameters may be executed on at least one beat of at least one lead. In another embodiment, the measurement may be executed on at least one beat of all available leads. In still another embodiment, the parameters may be measured on all the beats on at least one lead. In another embodiment, the measurement may be executed on all identified beats of all available leads. In still another embodiment, the measurement may be executed on a set of identified beats of individual leads selected by qualified person. In another embodiment, the measurement may be executed on at least one beat selected by the qualified person.

The measurement may provide at least one of following exemplary parameters on at least one beat in at least one lead: deviation of at least one axis; deviation of left axis; deviation of right axis; deviation of QRS axis; duration of at least one of P, Q, R, S, T and/or U deflection; identification of beat pattern including (including qR, qRs, Qr, qrS, QS, rS, RS, Rs, RSr', rSr', rSR', rsR', rR' and/or rsR's'); Q/R ratio; stability of at least one of P, Q, R, S, T, and/or U deflection; intervals between at least two of P, Q, R, S, T, and/or U deflections wherein interval may be defined as the start of the first deflection and the end of the second deflection; ST elevation and/or depth; depth of at least one of P, Q, R, S, T and/or U deflection; amplitude of at least one of P, Q, R, S, T and/or U deflection; QRS complex duration; heart rate and/or sinus pause.

The plurality of beats of at least one lead may be averaged by an averaging process and used for ECG analysis in an averaged manner. In order to provide visualization, averaged data may be subjected to measurement and the resulting averaged beat may be displayed to provide the qualified person with other information distinguished from the typical beat.

Selection of the typical beat may follow the measurement and may be accomplished by application of selection attributes. The typical beat may be selected as the beat reaching the best selection score in all available selection attributes. The typical beat may be selected as the beat reaching the best selection score in at least one selection attribute described below. Other beats may also be scored for the type of visualization described below. The selection attributes of the typical beat may include signal/noise ratio, QRS complex width, ST segment duration, ST interval duration, QT interval duration, PR segment duration, PR interval duration, PQ interval duration, presence of U deflection, amplitude height of QRS deflections, beat pattern, RR duration RR duration, RR interval stability, QRS axis and/or others. Preferred attributes used for selection of the typical beat may be at least one, more preferably at least two of these attributes. Even more preferred set of attributes may be signal/noise ratio, RR duration and at least one other mentioned selection attribute. Most preferred set of attributes may be signal/noise ratio, RR duration, amplitude height of QRS deflections and the most frequent QRS complex width present in all QRS complexes present in at least one lead.

The system and method may select the typical beat by application of at least one selection attribute. The attribute or attributes may include a scale of importance applied during the selection. The scale of importance of any individual attributes may be changed by the qualified person.

Selection of the typical beat through the application of the attributes may be executed on the plurality of the beats of an individual lead by implemented software comparison to find the typical beat for all the leads. The typical beat may be a group of the same beats on various leads. Also, the typical beat may be a representation of one beat on at least one or three or twelve leads. Therefore, using e.g. 12 lead ECG and finding the typical beat, allows viewing the electrical vector of the typical beat from 12 different positions. In an alternative embodiment, the typical beat may be established for each lead separately. In another alternative embodiment, the qualified person may preselect the plurality of the beats from any available leads in order to create a base for selection of the typical beat.

When the typical beat cannot be selected due to low quality of the ECG signal, the system will not allow the continuation of the procedure and inform the qualified person to repeat ECG signal recording. For example, the low quality of the ECG signal may be characterized by high power interference noise from motion artifacts, muscle artifacts, power line interference and/or EMG from the chest wall.

It may be also executed on the plurality of the beats of the plurality of available leads. In another embodiment, the typical beat may be selected directly by a qualified person as a one particular beat.

In still another embodiment, the qualified person may select a one or more beats from any individual lead to create a basis for typical beat selection. This may allow the qualified person to focus on a beat and/or a typical beat of a plurality of beats with minor alterations which are not visible at other beats.

Calculated parameters of all beats may be then stored in a storage unit and compared to the at least one criterion in next step of the diagram.

In another embodiment the selection of typical beat is not required and the selected set of criterions may be compared with the measured parameters of any beat and/or the set of a beats selected by a qualified person from the all beats of all leads. It may allow the qualified person to focus on every single beat and/or the whole set of beats without a necessity to obtain a typical beat.

Detection of the beats, measurement of the beats, selection of the typical beat, and signal recording and signal processing, may be evaluated during the evaluation 24 in order to ensure the quality of the results. In another embodiment, the evaluation may be executed during the whole process of ECG analysis immediately after each event of the block in the block diagram. It may also signal the need for new measurement to the qualified person by any human perception form. Alternatively, the new measurement may immediately follow after the evaluation of an imperfection.

Parameters calculated during the signal analysis may be then subjected to relation to criterions 25, which may be predetermined to fit the characteristic of the possible alterations and/or diseases of the heart and/or another body system. Parameters are compared to the limits of at least one of the criterions and the subsequent results may be used to visualize the abnormality of the signal on the display. The method and system may provide a diagnosis suggestion 26, which may aid the qualified person with the diagnosis conclusion. According to still another embodiment, the method and system may provide a diagnosis conclusion.

As many parameters may be measured on every available beat, the system and/or the qualified person may select the typical beat to enable significant reduction of time. In the preferred embodiment the measured parameters may be compared with the plurality of criterions. In the preferred embodiment the system and method compares criterion or criterions on at least 3 leads of the ECG system, more preferably on at least 5 leads of the ECG system, most preferably on at least 12 leads of the ECG system and the total number of criterion comparisons is at least 3, more preferably at least 5, even more preferably at least 12 and most preferably at least 18. Criterions used to predict possible risk may be selected for example from the set of criterions related to the athletic youth, Brugada syndrome criterions or any other criterions used by medical professionals. Criterions used to predict possibility of risk may be selected from the set of criterions related to sudden cardiac death syndrome. In another embodiment, the qualified person may add a new set of proposed criterions to an already existing set or create a new set of criterions to obtain a new form of ECG data analysis that may be helpful in diagnosis of the another alteration and/or disease.

Systems and methods of the invention may also produce information about the presence of a pacemaker implanted in the body of the patient, wrongly positioned ECG electrodes and/or other technical irregularities of the ECG recording. This information may be provided during the execution of any block mentioned in the block diagram illustrated by FIG. 2.

In the preferred embodiment the typical beat may not be produced by any averaging process, but may be selected from the plurality of identified and measured beats from filtered signal. Therefore, typical beat may be produced and/or selected from non-averaged signal. However, according to still another embodiment, the typical beat may include also an averaged beat. The automated selection of typical beat may be also changed to another selection of typical beat by a qualified person. In that case, all parameters related to the typical beat may be automatically recalculated to fit the newly selected beat and compared to the limits of the predetermined criterions. In still another embodiment, the qualified person may select a set of beats to create a basis for typical beat selection. In still another embodiment beats may be selected by a qualified person to create an amendment to already selected typical beat. Amended beats may be visualized in a superimposition to the typical beat.

Final results of the analysis and proposed diagnosis suggestion may be transferred to a Hospital Information System database where the ECG data and analysis may be further studied and/or corrected by the qualified personnel.

In the case the beat of interest may not be detected correctly or the typical beat may not be detected at all, the qualified person may use calipers to identify at least one basic parameter of the beat. The algorithm may execute detection of all other parameters of the newly designated beat. Therefore the measurement of the parameters may be executed repeatedly in independent manner from the block diagram illustrated on FIG. 2. In a preferred embodiment, the basic parameters may include the width of QRS complex, RR duration, ST segment width, length of ST interval, length of QT interval, length of PR segment, length of PR interval and length of PQ interval.

Figure 3:
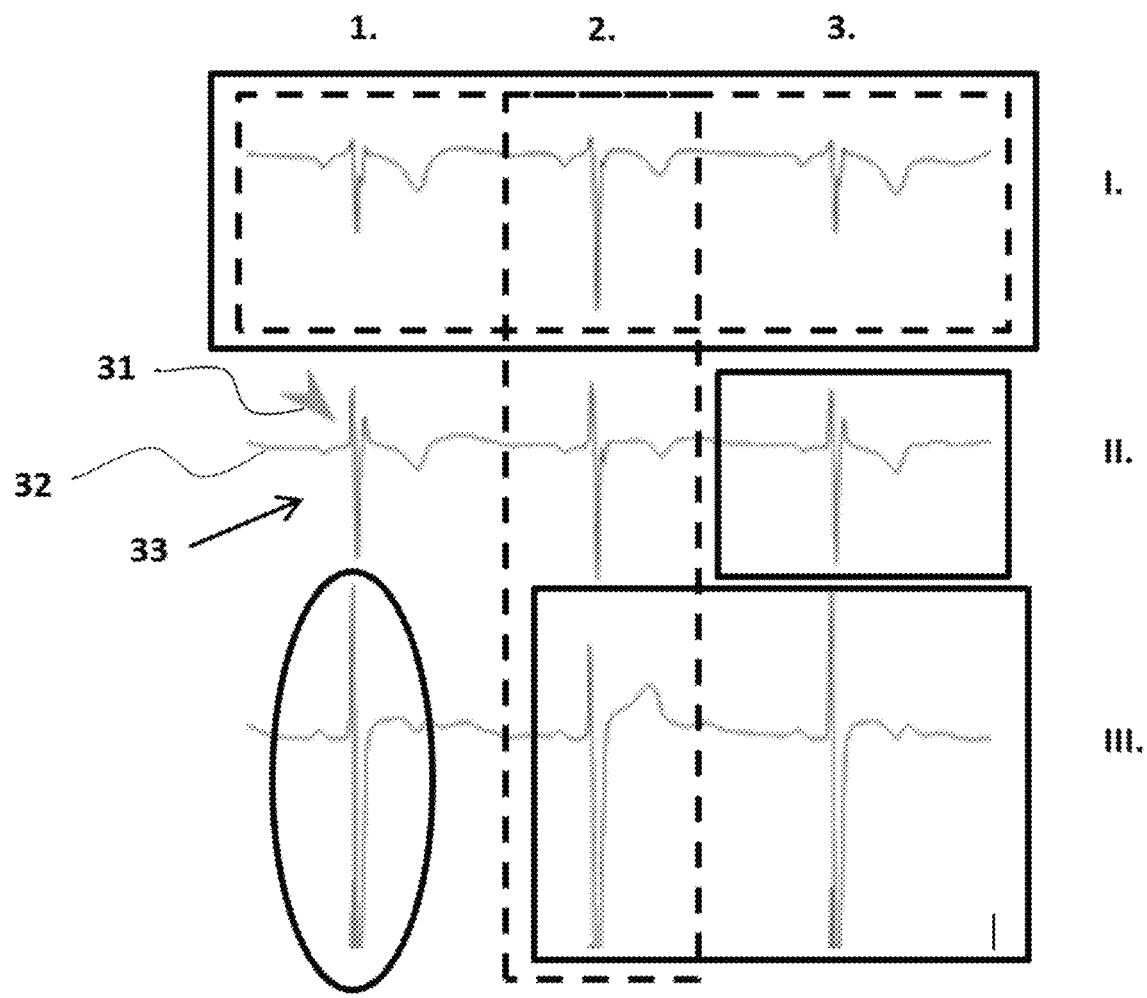
FIG. 3 is an exemplary illustration of a visualization of the analyzed ECG data.

Referring to FIG. 3, the typical beat may be selected from:

1. The beats of one lead (in the horizontal direction along the time axis) as indicated by the horizontal rectangle shown in both solid and dotted lines in FIG. 3.

2. The plurality of beats of all available leads (in the vertical direction along the voltage axis) as indicated by the vertical rectangle shown in dotted lines in FIG. 3.

3. The plurality of beats of all available leads selected at random, as indicated by the rectangles in FIG. 3.

4. By the direct selection of the typical beat (e. g. by a qualified person) as indicated by the ellipse in FIG. 3.

The typical beat may be represented by signals for one beat on all leads and/or at least one selected lead, wherein signals are beats from filtered signal. Therefore the representation shown on FIG. 3 by the vertical dotted rectangle may be representation of such typical beat shown on all available leads.

These different forms of the typical beat may be selected from the same ECG signal. Therefore the individual ECG recording may provide different sets of typical beats.

After the diagnosis suggestion 26, the graphic representation 27 with all the related features of visualization described below may be shown. Also, the graphic representation may be part of diagnosis suggestion 26 and/or diagnosis conclusion.

FIG. 3 illustrates an exemplary visualization of three vertical groups of beats (1, 2 and 3) sequenced on the ECG signals from three leads. This type of visualization may display the ECG signal 32 with the representation of some measured parameters related to the beat 33 and/or plurality of beats and/or the signal itself. The displayed beats may be marked (e.g. by a symbol 31) to express critical, non-critical and/or frontier characteristics of their relation to a possible irregularity of their at least one measured parameter compared to a set of criterions. The displayed beats may be marked to express a critical and non-critical characteristic of at least one measured parameter. The visualization of different marks may distinguish between critical and/or non-critical breach or may distinguish between typical beat and beat.

The possible marking may include different coloring of every beat, symbol in the vicinity of the anomalous beat or particular part of the waveform and any other human perception form. The beat may be also marked by an arrow, as shown in FIG. 3. The marking 31 itself may draw attention of the qualified person to a problematic part of the ECG signal 32. In one embodiment the marked typical beat may be zoomed-in to visualize its anomalous attributes. In another embodiment the marked beat may be selected for detailed analysis without necessarily designating it as a typical beat, since not all of the criterion may be necessarily compared with the typical beat.

Figure 4:
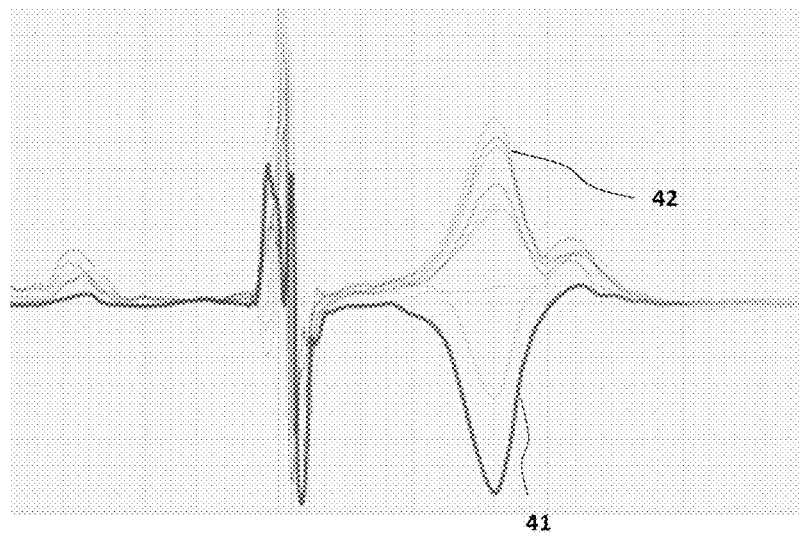
FIG. 4 is an exemplary illustration of a visualization of a typical beat superimposed on other beat.

FIG. 4 illustrates an exemplary superimposition of the typical beat 41 on at least one other beat 42. According to the exemplary embodiment shown in FIG. 4, the typical beat 41 may be partially superimposed on at least one beat from the other lead or leads. However, the typical beat 41 may also be partially superimposed by at least one other beat from the same lead. In exemplary embodiment the typical beat 41 may be shown in solid line with no transparency superimposed by at least one beat 42 from at least one of the individual leads. In still another embodiment the typical beat may be superimposed by beats selected by random manner according to wishes of qualified person. The displayed other beats may be shown with a certain level of transparency distinguishing themselves from the typical beat displayed by solid line. The transparency of other beats may be based on plurality of the factors. The preferred set of factors is the selection score described above, a parameter similarity of other beats to the typical beat and/or a parameter similarity of the individual deflection of other beats to the typical beat.

A more preferred set of factors is the selection score described above, the similarity of amplitude value of QRS deflection to the typical beat and the similarity of the QRS width to the typical beat. The most preferred factor is the selection score described above.

In one embodiment, the parts of superimposed beats with the exact overlay may be colored differently (e.g. different color, hue, luminance, saturation etc.) from the rest of the beats.

According to another example, when the typical beat is at any part superimposed by at least one beat, the almost exactly superimposed parts of both beats may be marked by different colors. The other part of the compared beat may be marked by red color to draw attention of qualified person to this particular part.

In another embodiment, the superimposition of the beats may be supplied with a text list of displayed beats. This list may serve to select another displayed beat other than typical beat. Selection of a different beat may be demonstrated by change of transparency. The newly selected beat may therefore be visualized as new solid beat. The typical beat may be therefore also displayed with certain degree of transparency, but without missing the typical beat status.

In still another embodiment, the anomaly in any visualized beat may be marked by an optional marking, which may include colored arrows, colored circles, colored parallel lines and other. The displayed marking may also share the degree of transparency according to marked beat.

This type of visualization may be advantageous for the qualified person because the superimposition of the signal provides information about other beats. As has been already noted, the non-averaged signal may include all beats with all their anomalies and provides the more broad information about the function of the heart. Using the described superimposition, the qualified person may focus attention on the typical beat visualized with no transparency. At the same time, the qualified person may also observe other beats possessing certain degrees of transparency. Such visualization may allow comparing the typical beat to another beat and noticing anomalies of other beats. In contrast to the standardized averaged beat analysis where the averaged beat is created from all beats, the typical beat may be one of recorded beats and still, it represents all other beats in the best possible manner. The visualization of the typical beat does not prevent the qualified person from deep analysis of other beats, which may lead to more precise diagnosis. This aspect is further strengthened by possible change of the transparency of the beats by a qualified person. Therefore the proposed superimposition provides advantage over analog reports printed on graph paper. The superimposed beats may be assessed and analyzed in significantly shorter time than the graph paper report.

It should be understood that the described features of visualization of beats may help the qualified person to compare all displayed leads, therefore the visualization may aid in selection of more precise diagnosis suggestion.

Figure 5:
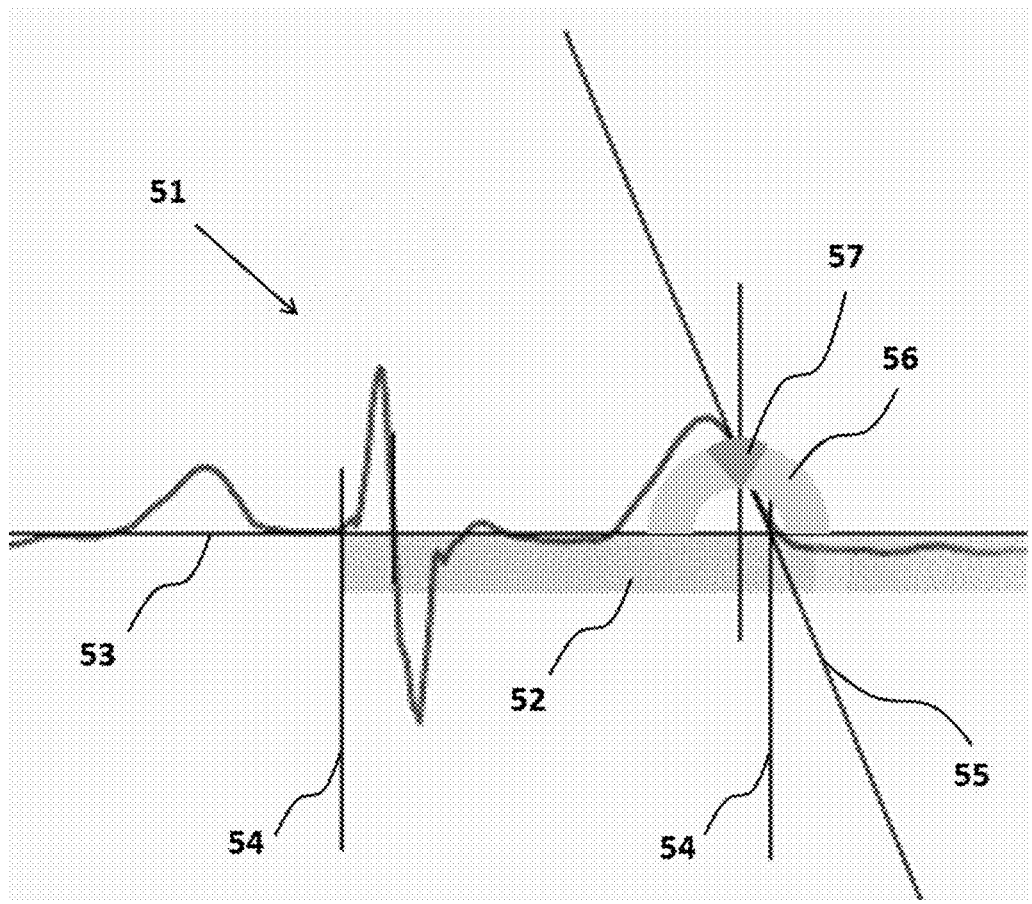
FIG. 5 is an exemplary illustration of a visualization of the single beat with a measuring device.

FIG. 5 illustrates an exemplary visualization of the beat 51 with a positionable measuring device 52, which may include a ruler, protractor, circular sector, French curve, tangent line, circle and the like. The measuring device may be able to visualize the measured parameter and/or the criterion in order to clearly inform the qualified person. The measuring device may comprise a measuring parameter scale and/or criterion scale. More preferably the measuring device may provide visualized information about various levels of criterion satisfaction. As an example, the measured non-critical parameters which are clearly out of the criterion's breach may be visualized by green color, the measured frontier parameters which are close to the criterion breach may be visualized by yellow color and the measured critical parameters which breach the criterion may be visualized by red color. The proposed system and method may be possible to display at least one measuring device. The measuring device may be displayed e.g. on horizontal axis, vertical axis, in angle or close to the measured waveform to the ECG signal. The beat may be a typical beat and/or zoomed-in individual beat selected by the qualified person.

In an exemplary embodiment the ruler 52 may be displayed in a horizontal manner under the baseline 53 to aid the qualified person with evaluation of the possible breach of the limits of the criterion testing the length of QT interval bordered by the calipers 54. Another exemplary shown element is the tangent 55 used to indicate the end of the T wave. The ruler may 52 be composed of a green element and a red element, where the green element marks the normal part of the tested parameter and the red element marks the breach of the limits of the criterion and an abnormal part of the parameter. In addition, the ruler may also include the yellow part marking the border lines of normality/abnormality, and therefore it may show the part of the ECG signal suspected of not meeting the limits of criterion. Another exemplary element shown is the tangent 55 used to indicate the end of the T wave. The semicircle 56 may include a circular sector 57 marking the border lines of normality/abnormality.

In another embodiment, the ruler may be displayed in a vertical manner. For example, the vertical ruler may aid with the evaluation of the possible breach of the limits of the criterion testing the depth of Q deflection. The displayed colored ruler may show the normal and abnormal depth of the tested parameter and aid the qualified person with a diagnosis suggestion concerning the pathologic shape and depth of the Q deflection.

In still another exemplary embodiment the French curve may be displayed in the vicinity of the ECG signal. It may aid the qualified person with determination of the unwanted curvature of the baseline. This may aid with the identification of the irregularities of amplitude height.

A displayed beat may be zoomed-in to display individual regions of the beat. It may be combined with already described embodiment concerning the visualization of the results.

The measuring devices may be displayed on visualization shown on FIG. 3. The measuring devices may be displayed independently for every beat of any lead.

Operation of the system may be improved based on corrective actions executed by the qualified person. The system may track the manual settings of the positions of the calipers, and correction of the measurement and/or the identification of the wave deflection. The system may also evaluate the selection of the typical beat and/or the selection of individual beat to improve the selection method. In addition, the system may boost evaluation by using data concerning the correction and/or denial of a suspected breach of the limits of at least one criterion.

The proposed system and method may be used for prediction of a suspected sudden death syndrome by comparing measured parameters to predefined sets of criterions. Also, the system and method may be used for increasing awareness of a possible sudden death syndrome to patient. Similarly, the system and method may be used for notification of possibility of sudden death syndrome. One particular group may be a set of criterions related to athletic and relatively healthy young population undergoing an intense training.

Subsequent changes in heart physiology and instabilities of the ECG signal linked to respiratory rate observed in athletic young population are the main aspects prohibiting usage of averaged ECG to obtain diagnosis suggestion. The ECG waveforms may be influenced by breathing. During breathing the heart rate may vary. Mainly during the inspiration phase, the heart rate accelerates PR and QT intervals are reduced and amplitudes of QRS deflections are changed. On the other hand, during the expiration phase, the heart rate slows. Described anomalies may occur mainly in young populations and athletic populations. Therefore there is a need to provide a system and method for choosing a typical beat, which does not represent heart rate extremities.

Application of the criterions to predict the sudden death syndrome may include recording of the heart electrical activity by standard 12-lead ECG configuration. The individual beats are detected according to the above described method. In one embodiment the method may require identification of typical beat, which is selected from all recorded beats of the individual lead. It also means that the selection process may select a set of typical beats according to their respective leads.

The deflections of the ECG signal are subjected to signal measurement to provide a set of parameters. In one embodiment the measurement may be executed on all beats of all leads. In another embodiment the measurement may be executed on all beats of the selected at least one lead. In another embodiment the measurement may be executed on all leads of the at least one beat. In still another embodiment the measurement may be executed on at least one selected beat of at least one selected lead.

The comparison of the at least one parameter to at least one of the criterions results in the visualization of possible critical parts of ECG signal and/or diagnosis suggestion.

As an example, the parameter characterizing length of QRS complex duration may be compared to the criterion defining intraventricular conduction delay. When the time of duration exceeds for example 140 ms, the parameter breaches the limits of the criterion and the criterion is declared as positive. One positive criterion may be assessed as the positive result of the ECG screening and the patient may be under risk of the sudden death syndrome. The beat characterized by anomalous QRS complex duration may be visualized according to the preference of a qualified person.

The qualified person may not agree with the results of the ECG data analysis related to criterions. The qualified person may visualize the ECG signal together with the measuring device and criteria wording, then change the selected typical beat, correct the measured parameter (e.g. by calipers) and/or declare the related criterion as positive or negative. When the typical beat is changed to another beat, the parameters related to the ECG data may be compared to the criterions and new results may be visualized.

In another exemplary embodiment, the system and method may be used to aid in diagnosis of Brugada syndrome. Criterion described may encompass a proposed set of criterions used to diagnosis of this heart disease.

In another exemplary embodiment, the system and method be used to aid in prediction of the sudden infant death syndrome and others.

In another exemplary embodiment, the system and method be used to aid in prediction of the myocardial infarction and others.

An exemplary embodiment of the method may include application of the electrodes on the patient's body to provide standard 12-lead ECG. Further, the embodiment may use the scheme shown on FIG. 1B.

ECG recording may be executed by a standard 12-lead system. Signal recording may undergo signal processing and then be provided to the display or to the external device, alternatively the recorded data may directly communicated to the external device for EC signal processing. Also, ECG data may be stored in the memory and analyzed later.

According to the exemplary embodiment of the method the signal processing may include filtering of the signal immediately after the data recording.

Signal analysis may include detection of the beats by the combination of three leads and subsequent application of an adaptive algorithm searching for the global and/or local maxima of the signal. Subsequent measurement may provide plurality of different parameters, wherein all parameters are measured on all identified beats of all available leads.

In one exemplary embodiment the typical beat may then be selected by application of selection attributes from all recorded beats. In this specific embodiment the typical beat is selected according to QRS complex width, signal/noise ratio and amplitude height of QRS complexes. The typical beat is selected as beat with highest score of all selection attributes according to scale of attributes, wherein the provided order of the selection attributes disclose the priority of one selection attributes over the others. Therefore, beat with lower signal/noise ratio would have better score than a beat with higher amplitudes of QRS complexes.

Figure 6A:
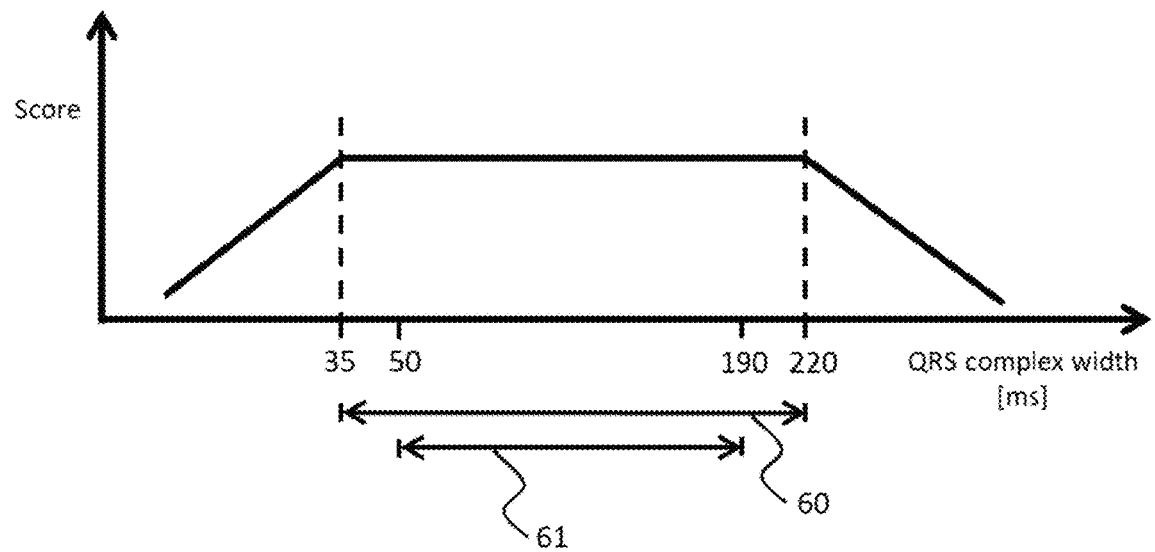
FIG. 6A is an exemplary distribution of QRS complex width related to score.

The QRS complex width used for selection of typical beat may be the most frequent QRS complex width present of all QRS complexes in recorded ECG signal. Also the QRS complex width used for selection of typical beat may be the widest QRS complex width present in recorded ECG signal. The QRS complex width used for selection of typical beat may be in the range of 35 ms to 220 ms or 40 ms to 200 ms or 50 ms to 190 ms or 55 ms to 185 ms. The QRS complex width within these ranges may be claimed as the one with the highest score. Each deviation may mean decrease of the score e.g. minus one, two or more points for each at least 1, 2, 5 or more ms. Also the highest score QRS complex width may be maximally in the range of 35 ms to 220 ms or 50 ms to 190 ms or 55 ms to 185 ms or narrower. As shown in FIG. 6A the interval 60 is the range of 35 ms to 220 ms, while interval 61 is the range of 50 ms to 190 ms and therefore is narrower and lays in the maximal range of the depicted interval 60.

Figure 6B:
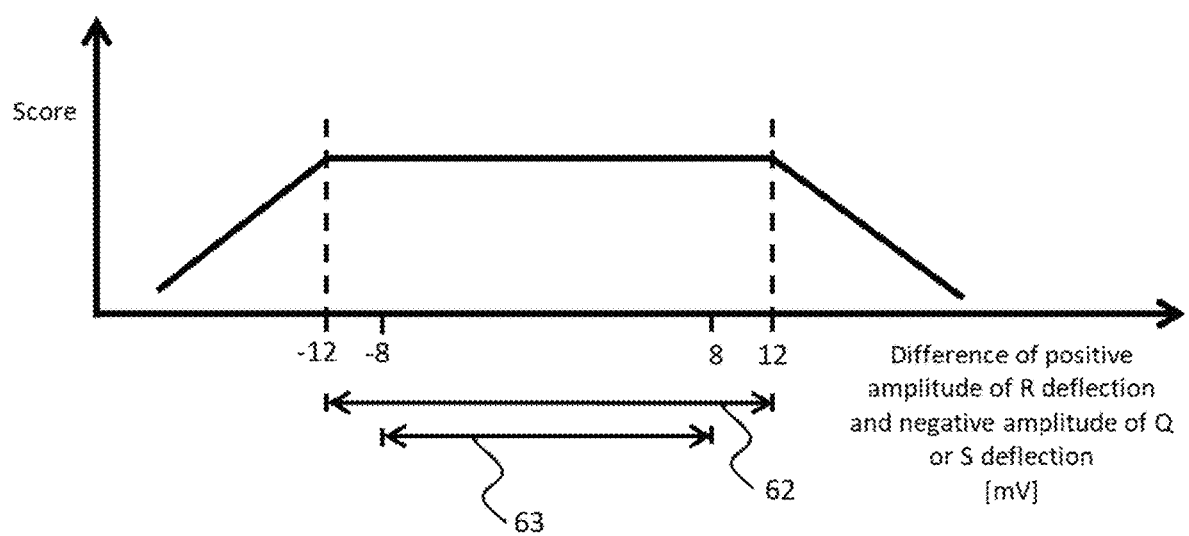
FIG. 6B is an exemplary distribution of difference of positive amplitude of R deflection and negative amplitude of Q or S deflection related to score.

Selection attribute of amplitude heights of QRS complexes may include selection of beats with highest amplitudes of at least one deflection. Also, selection attribute of amplitude heights of QRS complexes may include beats with highest amplitude of Q, R and/or S deflections. Additionally, this selection attribute may include selection of beat having the highest difference of positive amplitude of R deflections and one of negative amplitudes of Q or S deflections. Further, this selection attribute may include selection of beat having the highest difference of positive amplitude of R deflection and negative amplitudes of Q deflection, when the S deflection of the beat has deeper amplitude than Q deflection. Furthermore, this selection attribute may include selection of beat having the highest difference of positive amplitude of R deflections and negative amplitude of S deflection, when the Q deflection of the beat has deeper amplitude than S deflection. In all cases, the difference may be in the range of −12 mV to 12 mV or −10 mV to 10 mV or −8 mV to 8 mV or −6 mV to 6 mV. The amplitude height within these ranges may be claimed as the one with the highest score. Each deviation may mean decrease of the score e.g. minus one, two or more points for each 0.1, 0.2 0.5 or more mV. Also the highest score amplitude height of QRS complex may be maximally in the range of −12 mV to 12 mV or −10 mV to 10 mV or −8 mV to 8 mV or −6 mV to 6 mV. As shown on FIG. 6B the interval 62 is the range of −12 mV to 12 mV, while interval 63 is the range of −8 mV to 8 mV and therefore is narrower and lays in the maximal range of the depicted interval 62.

Figure 6C:
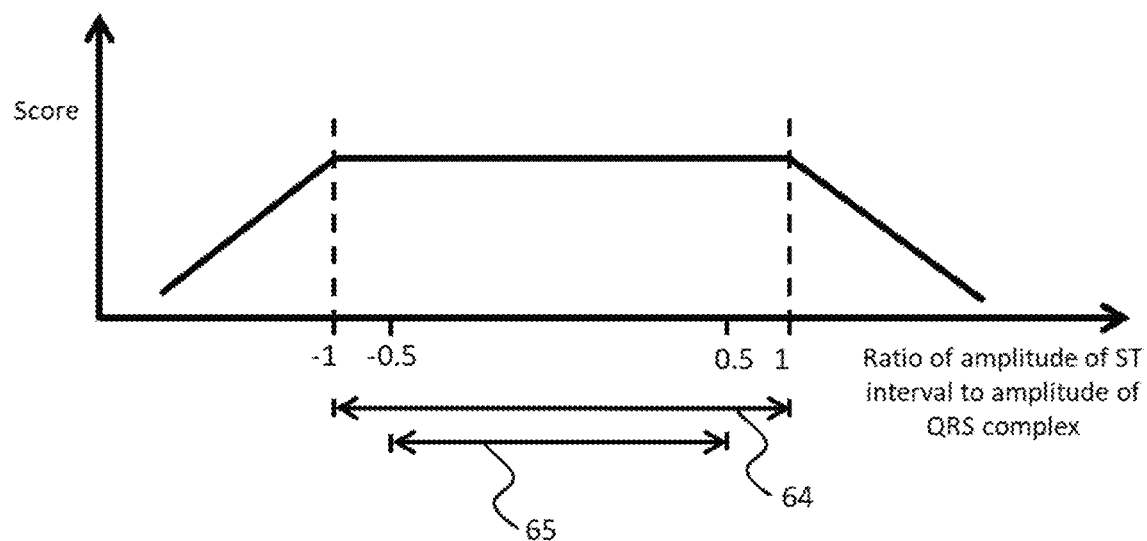
FIG. 6C is an exemplary distribution of ratio of amplitude of ST interval to amplitude of QRS complex related to score.

The signal/noise ratio may include calculating of signal/noise ratio of PQ interval and its subsequent comparison with signal/noise ratio of QRS complex. In another embodiment the signal/noise ratio may include ratio of the average power of the signal and the average power of background noise. In still another embodiment the signal/noise ratio may include ratio of amplitude of ST interval to amplitude of QRS complex, wherein amplitude of ST interval may mean possible elevation between end of S deflection and start of T deflection and amplitude of QRS complex may mean difference of positive amplitude of R deflections and one of negative amplitudes of Q or S deflections. The signal/noise ratio and/or ratio of amplitude of ST interval to amplitude of QRS complex may be in the range of −1 to 1 or −0.5 to 0.5 or −0.2 to 0.2. The signal/noise ratio within these ranges may be claimed as the one with the highest score. Each deviation may mean decrease of the score e.g. minus one, two or more points for each 0.01, 0.02 0.05 or more. Also the highest score signal/noise ratio may be maximally in the range of −1 to 1 or −0.5 to 0.5 or −0.2 to 0.2. As shown on FIG. 6C the interval 64 shows the range of −1 to 1, while interval 65 shows the range of −0.5 to 0.5 and therefore is narrower and lays in the maximal range of the depicted interval 64.

In another embodiment the typical beat may then be selected by application of selection attributes from all recorded beats. In this specific embodiment the typical beat is selected according to QRS complex width, signal/noise ratio, beat pattern, RR duration and amplitude height of at least one beat deflection. The typical beat is selected as beat with highest score of all selection attributes according to scale of attributes, wherein the provided order of the selection attributes disclose the priority of one selection attributes over the others. Therefore, beat with lower signal/noise ratio would have better score than a beat with higher amplitudes of QRS deflections. The QRS complex width used for selection of typical beat may be the most frequent QRS complex width present in recorded ECG signal. Also the QRS complex width used for selection of typical beat may be the widest QRS complex width present in recorded ECG signal. Selection attribute of amplitude heights of beat deflections may include selection of beats with highest amplitudes. Also, selection attribute of amplitude heights of beat deflections may beats with highest amplitude of Q, R and/or S deflections.

The typical beat may be one beat on all available leads, most typically all twelve leads. After the evaluation, the measured parameters related to the typical beat may be subjected to relation to criterions and visualized.

In one exemplary embodiment, at least one criterion from following table may be used for relation of parameter. When the analyzed ECG signal includes at least one parameter fulfilling following criterions the method and device may provide diagnosis suggestion and/or the diagnosis conclusion.

| Name of ECG criterion | Definition of criterion |
| --- | --- |
| Ventricular arrhythmias | Couplets, triplets and non-sustained ventricular tachycardia |
| Premature ventricular contractions | ≥2 premature ventricular contractions per 10 s tracing |
| Atrial tachyarrhythmias | Supraventricular tachycardia or atrial fibrillation or atrial flutter |
| Profound sinus bradycardia | <30 beats per minute or sinus pauses ≥3 s |
| Brugada-like ECG pattern | High take-off and downsloping ST segment elevation followed by a negative T wave in ≥2 leads in V1 to V3 |
| Prolonged QT interval | Marked QT prolongation - QTc ≥500 ms or male: QTc ≥470 ms or female: QTc ≥480 ms |
| Short QT interval | QTc ≤320 ms |
| Ventricular pre-excitation | PR interval <120 ms with a delta wave (slurred upstroke in the QRS complex) and wide (>120 ms) |
| Right ventricular hypertrophy pattern | (|R in V1| + |S in V5|) >10.5 mm and right axis deviation >120°; wherein |R-V1| means position of R deflection in lead V1 and |S in V5| means position of S deflection in lead V5 |
| Intraventricular conduction delay | Any QRS duration ≥140 ms |
| Complete left bundle branch block | QRS ≥120 ms and predominantly negative QRS complex in lead V1 (QS or rS) and upright monophasic, notched or slurred R wave in leads I and V6 |
| Pathological Q waves | Q wave >3 mm in depth or width of Q wave >40 ms in two or more leads (except for III and $aV_R$) |
| ST segment depression | ≥0.5 mm in depth in two or more, preferably contiguous leads |
| T-wave inversion | ≥1 mm in depth in two or more leads V2-V6, II and $aV_F$, or I and $aV_L$ (excluding leads III, $aV_R$, and V1); more preferably at least one of combination of leads provided below: leads V2-V4; I and $AV_L$, leads V5 and/or V6 leads II and $aV_F$, V5-V6, I and $AV_L$ leads II and $AV_F$ |

-continued

| Name of ECG criterion | Definition of criterion |
|---|---|
| Left axis deviation | −30° to −90° |
| Left atrial enlargement | Prolonged P wave duration of >120 ms in leads I or II with negative portion of the P wave ≥1 mm in depth and 40≥ms in duration in lead V1 |
| Right axis deviation | >120° |
| Atrioventricular block | Pathological atrioventricular block: 2° atrioventricular block (including Mobitz type I) or complete 3°atrioventricular block |
| Profound 1° atrioventricular block | PR interval ≥400 ms |
| Brugada type 1 pattern | Coved pattern including initial ST elevation ≥2 mm (high take-off) with downsloping ST segment elevation followed by a negative symmetric T wave in more than 1 leads in V1-V3 |
| Epsilon wave | Distinct low amplitude signal (small positive deflection or notch) between the end of the QRS complex and onset of the T wave in leads V1-V3 |
| Pathological Q waves | Q/R ratio ≥0.25 ms or ≥40 ms in duration in two or more leads (excluding III and $aV_R$) |

QT means measure of the time between the start of the Q wave and the end of the T wave, QTc means corrected QT, wherein correction is by using a Bazett's formula, Fridericia's formula and/or Sagie's formula. Also, Qs means recorded large wave Q and smaller wave S, while rS means small wave r and larger wave S.

Also some criterions may be used to show possibility of ECG abnormality by combination. When the analyzed ECG signal includes at least two parameters fulfilling the criterions from the group called "suspecting ECG criterions", the method may include diagnosis suggestion and/or the diagnosis conclusion. The following table shows criterions from the group of suspecting ECG criterions.

| Name of ECG criterion | Definition of criterion |
|---|---|
| Left axis deviation | −30° to −90° |
| Left atrial enlargement | Prolonged P wave duration of >120 ms in leads I or II with negative portion of the P wave ≥1 mm in depth and 40≥ms in duration in lead V1 |
| Right axis deviation | >120° |
| Right atrial enlargement | P wave >2.5 mm in II, III, or $aV_F$ |
| Complete right bundle branch block | rSR' pattern in lead V1 and an S wave wider than R wave in lead V6 with QRS duration ≥120 ms |

All the methods, aspects, embodiments and examples described above may be combined together.

If the methods described above result in a suggestion of a diagnosis of sudden cardiac death syndrome, additional steps may be performed. These include advising the patient to make certain lifestyle changes, which may include one or more of losing weight, change in diet, exercising, reducing physical and/or mental stress, stopping smoking or stopping use of un-prescribed drugs, and/or use of vagal manuevers. An additional step may also include conducting further tests on the patient, such as blood tests, echocardiogram, exercise stress tests, cardiac catheterization, MRI and MUGA. An additional step may include monitoring the patient, e.g., using a Holter monitor, an event monitor or an implantable loop recorder. Monitoring may also be provided via future periodic doctor visits. One or more medications maybe prescribed for the patient following a diagnosis of sudden cardiac death. The medications prescribed may include ACE inhibitors, beta-blockers, calcium-channel blockers, and other antiarrhythmics. For patients with high cholesterol and coronary artery disease, statin drugs may be prescribed. For some patients, an additional step may include interventional procedures or surgery of the heart, including for example, implanting a pacer/defibrillator or similar type of device in the patient, by-pass, Maze, or catheter ablation procedures.

The foregoing description of a preferred embodiment of the invention has been presented for purposes of illustration and description. It is not intended to be exhaustive or to limit the invention to the precise form disclosed. Modifications and variations are possible in light of the above teachings or may be acquired from practice of the invention. The embodiments described explain the principles of the invention and its practical application to enable one skilled in the art to utilize the invention. Various modifications as are suited to a particular use are contemplated. It is intended that the scope of the invention be defined by the claims appended hereto and their equivalents.

The invention claimed is:

1. A method for an ECG analysis for diagnosing a sudden death syndrome, comprising:
   positioning ECG electrodes on a patient's body; recording an ECG signal to an ECG monitoring device;
   filtering the ECG signal by performing at least one filtering step with a processor, the filtering step selected from the group consisting of removing baseline drift, removing motion artifacts, removing muscle artifacts, removing power line interference, and removing EMG from a chest wall;
   identifying a global and/or local maxima of the filtered ECG signal;
   detecting beats presented in the filtered ECG signal using a combination of at least two selected ECG electrodes and the identified global and/or local maxima of the filtered ECG signal;
   selecting a typical beat from the filtered ECG signal wherein the typical beat is the beat having a highest score of selection attributes as determined by at least one of (A) a QRS complex width, (B) a signal/noise ratio, and (C) an amplitude height of QRS complex; wherein
   (A) the QRS complex width is the most frequent QRS complex width of all QRS complexes present in the filtered ECG signal and wherein the highest score QRS complex width is maximally in the range of 35 ms to 220 ms;
(B) the signal/noise ratio is the ratio of amplitude of ST interval to amplitude of QRS complex, wherein amplitude of ST interval is the difference between end of S deflection and start of T deflection, and the amplitude of QRS complex is the difference of positive amplitude of R deflections and one of negative amplitudes of Q and/or S deflections, and wherein the highest score signal/noise ratio is maximally in the range of −1 to 1;
(C) the amplitude height of QRS complexes is the greatest difference of positive amplitude of R deflections and one of negative amplitudes of Q and/or S deflections, and wherein the highest score amplitude height of QRS complex is maximally in the range of −12 mV to 12 mV;
measuring the filtered ECG signal on the typical beat to determine a plurality of parameters of the typical beat, the plurality of parameters comprising a length of QRS complex duration;
providing a diagnostic suggestion of sudden cardiac death syndrome if the length of QRS complex duration exceeds 140 ms.

2. The method of claim 1 wherein the ECG signal is communicated from a processor to a memory.

3. The method of claim 1 wherein the electrodes are positioned into 12-lead placement.

4. The method of claim 3 wherein the typical beat is a representation of one beat on all leads.

5. The method of claim 1 further including providing visualization of the beats by using superimposition wherein the typical beat is superimposed by at least one beat from the same lead.

6. The method of claim 5 wherein a degree of transparency of the superimposition is based on at least one of selection score, similarity of amplitude value of QRS deflection to the typical beat and similarity of the QRS width to the typical beat.

7. The method of claim 6 wherein the visualization includes a positionable measuring device and a criterion scale.

8. A method for ECG analysis for diagnosing a sudden death syndrome, comprising:
positioning ECG electrodes on a patient's body; recording an ECG signal to an ECG monitoring device;
filtering the ECG signal by performing at least one filtering step with a processor, the filtering step selected from the group consisting of removing baseline drift, removing motion artifacts, removing muscle artifacts, removing power line interference, and removing EMG from a chest wall;
identifying a global and/or local maxima of the filtered ECG signal;
detecting beats presented in the filtered ECG signal using a combination of at least two selected ECG electrodes and the identified global and/or local maxima of the filtered ECG signal;
measuring the filtered ECG signal to determine a plurality of parameters of the filtered ECG signal, the plurality of parameters comprising a length of QRS complex duration;
selecting a typical beat from the filtered ECG signal wherein the typical beat is the beat having a highest score of selection attributes as determined by at least one of (A) a QRS complex width, (B) a signal/noise ratio, and (C) an amplitude height of QRS complex; wherein
(A) the QRS complex width is the most frequent QRS complex width of all QRS complexes present in the filtered ECG signal and wherein the highest score QRS complex width is maximally in the range of 35 ms to 220 ms;
(B) the signal/noise ratio is the ratio of amplitude of ST interval to amplitude of QRS complex, wherein amplitude of ST interval is the difference between end of S deflection and start of T deflection, and the amplitude of QRS complex is the difference of positive amplitude of R deflections and one of negative amplitudes of Q and/or S deflections, and wherein the highest score signal/noise ratio is maximally in the range of −1 to 1;
(C) the amplitude height of QRS complexes is the greatest difference of positive amplitude of R deflections and one of negative amplitudes of Q and/or S deflections, and wherein the highest score amplitude height of QRS complex is maximally in the range of −12 mV to 12 mV;
providing a diagnostic suggestion of sudden cardiac death syndrome if the length of QRS complex duration exceeds 140 ms.

9. The method of claim 8 wherein the electrodes are positioned into 12-lead placement.

10. The method of claim 9 wherein the at least one parameter of the typical beat comprises Q/T ratio and/or P/R interval and/or right axis deviation.

11. The method of claim 10 further comprising the step of providing a diagnostic suggestion of sudden cardiac death syndrome if the Q/T ratio exceeds 0.25 ms or 40 ms, or if the P/R interval exceeds 400 ms, or if the right axis deviation exceeds 120°.

12. The method of claim 11 further including providing visualization of the beats by using superimposition wherein the typical beat is superimposed by at least one beat from the same lead.

13. The method of claim 12 wherein a degree of transparency of the visualization is based on at least one of selection score, similarity of amplitude value of QRS deflection to the typical beat and similarity of the QRS width to the typical beat.

14. The method of claim 13 wherein the visualization includes a positionable measuring device and a criterion scale.

15. A method for ECG analysis for diagnosing a sudden death syndrome, comprising:
positioning ECG electrodes on a patient's body into a 12-lead placement;
recording an ECG signal to an ECG monitoring device;
communicating the ECG signal from the ECG monitoring device to an external device;
filtering the ECG signal by performing at least one filtering step with a processor, the filtering step selected from the group consisting of removing baseline drift, removing motion artifacts, removing muscle artifacts, removing power line interference, and removing EMG from a chest wall;
identifying a global and/or local maxima of the filtered ECG signal;
detecting beats presented in the filtered ECG signal using a combination of at least two selected ECG electrodes and the identified global and/or local maxima of the filtered ECG signal;

measuring the filtered ECG signal to determine a plurality of parameters of the filtered ECG signal, the plurality of parameters comprising a length of QRS complex duration;
- selecting a typical beat from the filtered ECG signal wherein the typical beat is the beat having a highest score of selection attributes as determined by at least two of (A) a QRS complex width, (B) a signal/noise ratio, and (C) an amplitude height of QRS complex; wherein
  - (A) the QRS complex width is the most frequent QRS complex width of all QRS complexes present in the filtered ECG signal and wherein the highest score QRS complex width is maximally in the range of 35 ms to 220 ms;
  - (B) the signal/noise ratio is the ratio of amplitude of ST interval to amplitude of QRS complex, wherein amplitude of ST interval is the difference between end of S deflection and start of T deflection, and the amplitude of QRS complex is the difference of positive amplitude of R deflections and one of negative amplitudes of Q and/or S deflections, and wherein the highest score signal/noise ratio is maximally in the range of −1 to 1;
  - (C) the amplitude height of QRS complexes is the greatest difference of positive amplitude of R deflections and one of negative amplitudes of Q and/or S deflections, and wherein the highest score amplitude height of QRS complex is maximally in the range of −12 mV to 12 mV;
- providing a diagnostic suggestion of sudden cardiac death syndrome if the length of QRS complex duration exceeds 140 ms.

16. The method of claim 15 wherein the ECG signal is communicated from a processor to a memory.

17. The method of claim 16 further including providing visualization of the beats by using superimposition wherein the typical beat is superimposed by at least one beat from the same lead.

18. The method of claim 17 wherein the degree of transparency is based on at least one of selection score, similarity of amplitude value of QRS deflection to the typical beat and similarity of the QRS width to the typical beat.

19. The method of claim 15 wherein the typical beat is a representation of one beat on all leads.

20. The method of claim 19 wherein the superimposed beats are visualized with a degree of transparency based on a selection score.

* * * * *